United States Patent
Kobori (10) Patent No.: US 9,206,046 B2
(45) Date of Patent: Dec. 8, 2015

(54) REACTOR FOR DEHYDROGENATION OF ORGANIC COMPOUND, HYDROGEN PRODUCTION APPARATUS, AND HYDROGEN PRODUCTION PROCESS

(75) Inventor: Yoshihiro Kobori, Tokyo (JP)

(73) Assignee: JX NIPPON OIL & ENERGY CORPORATION, Tokyo (JP)

( * ) Notice: Subject to any disclaimer, the term of this patent is extended or adjusted under 35 U.S.C. 154(b) by 133 days.

(21) Appl. No.: 13/520,473

(22) PCT Filed: Dec. 7, 2010

(86) PCT No.: PCT/JP2010/071922
§ 371 (c)(1),
(2), (4) Date: Oct. 10, 2012

(87) PCT Pub. No.: WO2011/083653
PCT Pub. Date: Jul. 14, 2011

(65) Prior Publication Data
US 2013/0022536 A1    Jan. 24, 2013

(30) Foreign Application Priority Data
Jan. 6, 2010 (JP) .................... 2010-001208
Mar. 23, 2010 (JP) .................... 2010-066363

(51) Int. Cl.
C01B 3/02 (2006.01)
C01B 3/26 (2006.01)
(Continued)

(52) U.S. Cl.
CPC ............... *C01B 3/26* (2013.01); *B01D 53/229* (2013.01); *C01B 3/503* (2013.01); *C01B 3/505* (2013.01);
(Continued)

(58) Field of Classification Search
USPC ........................................... 423/648.1
See application file for complete search history.

(56) References Cited

U.S. PATENT DOCUMENTS 5,430,218 A * 7/1995 Miller et al. ................. 585/654
2003/0083534 A1* 5/2003 Gauthier et al. .............. 585/818
(Continued)

FOREIGN PATENT DOCUMENTS

JP  3-217227  9/1991
JP  5-317708  12/1993
(Continued)

OTHER PUBLICATIONS

Search report for EP Application No. 10 84 2166, mailed on Sep. 13, 2013.
(Continued)

*Primary Examiner* — Jennifer A Smith
*Assistant Examiner* — Anita Nassiri Motlagh
(74) *Attorney, Agent, or Firm* — Greenblum & Bernstein, P.L.C.

(57) ABSTRACT

A hydrogen production process and a reactor for dehydrogenation in which it is possible to mix hydrogen with a raw material for a dehydrogenation reaction easily and simply and suppress a reduction in the performance of a dehydrogenation reaction catalyst when hydrogen is produced by combining the dehydrogenation reaction of organic hydrides or the like with a hydrogen separation membrane. A flow-type reactor for dehydrogenation of an organic compound includes a hydrogen separation membrane selectively permeable to hydrogen; and a dehydrogenation catalyst for promoting a dehydrogenation reaction of an organic compound which can release hydrogen upon the dehydrogenation reaction, including: a reaction side area through which the organic compound can flow and which includes the dehydrogenation catalyst and a permeation side area which is separated from the reaction side area by the hydrogen separation membrane and through which hydrogen that has passed through the hydrogen separation membrane can flow.

5 Claims, 6 Drawing Sheets (51) Int. Cl.
  *B01D 53/22* (2006.01)
  *C01B 3/50* (2006.01)
  *C07C 5/367* (2006.01)
  *C07C 45/29* (2006.01)
  *H01M 8/06* (2006.01)
  *C07C 45/00* (2006.01)
  *B01J 23/40* (2006.01)
  *B01J 23/42* (2006.01)
  *B01J 23/755* (2006.01)

(52) U.S. Cl.
  CPC ............... *C07C 5/367* (2013.01); *C07C 45/002* (2013.01); *C07C 45/29* (2013.01); *H01M 8/0618* (2013.01); *B01D 2256/16* (2013.01); *B01J 23/40* (2013.01); *B01J 23/42* (2013.01); *B01J 23/755* (2013.01); *C01B 2203/0277* (2013.01); *C01B 2203/041* (2013.01); *C01B 2203/0405* (2013.01); *C01B 2203/048* (2013.01); *C01B 2203/107* (2013.01); *C01B 2203/1011* (2013.01); *C01B 2203/1023* (2013.01); *C01B 2203/1047* (2013.01); *C01B 2203/1058* (2013.01); *C01B 2203/1064* (2013.01); *C01B 2203/1252* (2013.01); *C07C 2521/04* (2013.01); *C07C 2521/06* (2013.01); *C07C 2521/08* (2013.01); *C07C 2521/10* (2013.01); *C07C 2521/12* (2013.01); *C07C 2523/42* (2013.01); *C07C 2523/44* (2013.01); *C07C 2523/46* (2013.01); *C07C 2523/755* (2013.01); *Y02E 60/50* (2013.01)

(56) References Cited

U.S. PATENT DOCUMENTS

2007/0202023 A1* 8/2007 Bessho et al. ................ 422/222
2009/0012341 A1* 1/2009 Brophy et al. ................ 585/659

FOREIGN PATENT DOCUMENTS

| JP | 11-319521 | 11/1999 |
| JP | 2004-131306 | 4/2004 |
| JP | 2005-281103 | 10/2005 |
| JP | 2006-225169 | 8/2006 |
| JP | 2008-081385 | 4/2008 |

OTHER PUBLICATIONS

Kenji Yamaji ed., "Hydrogen Energy Society", Japan Society of Energy and Resources, May 26, 2008, p. 9, with partial English-language translation thereof.

Masaru Ichikawa, "Development of Hydrogen Storage and Supply Device by Organic Hydride Technology", Engineering Materials, vol. 51, No. 4, 2003, pp. 62-69, with partial English-language translation thereof.

Yoshimi Okada et al., "Development of Dehydrogenation Catalyst for Hydrogen Storage and Transportation System by the Organic Chemical hydride Method", Engineering Materials, vol. 31, No. 2, 2006, pp. 8-13 with partial English-language translation thereof.

Ito Naotsugu et al., "Application for Hydrogen Manufactory Reaction and Hydrogen Separation by Palladium Membrane", Engineering Materials, vol. 51, No. 4, 2003, pp. 74-76, with partial English-language translation thereof.

International Search Report issued with respect to PCT/JP2010/071922, mailed Mar. 22, 2011.

English-language translation of International Preliminary Report on Patentability issued with respect to PCT/JP2010/071922, mailed Aug. 23, 2012.

* cited by examiner

REACTOR FOR DEHYDROGENATION OF ORGANIC COMPOUND, HYDROGEN PRODUCTION APPARATUS, AND HYDROGEN PRODUCTION PROCESS

TECHNICAL FIELD

The present invention relates to a reactor for dehydrogenation, a hydrogen production apparatus, and a hydrogen production process for producing hydrogen by dehydrogenating an organic compound.

BACKGROUND ART

Hydrogen is widely used in various industrial fields such as petroleum refining and chemical industry. Especially, hydrogen has recently attracted attention as a future energy medium, and studies on hydrogen have been conducted with a focus on the field of fuel cells. However, it becomes a great barrier against spread of the hydrogen energy that transportation and storage of hydrogen are difficult (see Non Patent Literature 1 below).

Hydrogen gas is a voluminous fuel having a large volume per unit of heat amount, and combustion heat of the hydrogen gas at 1 atm (0.1 MPa) is only 1/3000 of that of gasoline having the same volume. Therefore, there are conducted transportation and storage of hydrogen whose energy density is increased by means of compression at an extremely high pressure such as about 35 MPa or 70 MPa. However, there is a problem that the cost of a device required for compression of hydrogen such as a compressor for hydrogen or a high-pressure container for compressed hydrogen is high. Moreover, it is expected that development of infrastructure for supplying hydrogen whereby safety of the compressed hydrogen can be ensured needs enormous cost.

Also, a technique concerning transportation and storage of liquefied hydrogen has attracted attention. However, it is necessary for liquefaction of hydrogen to cool hydrogen to a very low temperature such as about −253° C. Therefore, an extremely high-performance and expensive insulating container is required for transportation and storage of liquefied hydrogen. Furthermore, since energy required for the liquefaction of hydrogen is high, there is a problem of a decrease in energy efficiency associated with the liquefaction of hydrogen.

In order to overcome the aforementioned problem concerning transportation and storage of hydrogen, various hydrogen storage materials such as hydrogen storage alloys have been developed and studied; however, a material having a satisfactory performance has not been found yet.

As a medium used for transportation and storage of hydrogen, an organic compound which forms an unsaturated bond by a dehydrogenation reaction and at the same time releases hydrogen has attracted attention. A representative example thereof includes organic hydrides such as methylcyclohexane. When the organic hydrides are used as the medium, it is possible to store hydrogen in the organic hydrides which are liquid at room temperature, and therefore, it is expected that the cost of constructing infrastructure for transportation and storage can be reduced (see Non Patent Literature 2 below). It is noted that a dehydrogenation catalyst is generally used in the dehydrogenation reaction of the organic compound. In order to prevent a reduction in activity of the dehydrogenation catalyst, especially a reduction in activity due to carbon precipitation, it is effective to add 5 to 20 mole % of hydrogen to the organic compound before the dehydrogenation reaction (see Non Patent Literature 3 below).

In Non Patent Literature 4 below, it is proposed that generation and purification of hydrogen are conducted effectively by combining a technique concerning the dehydrogenation reaction of methylcyclohexane, or the like with a hydrogen separation membrane in which a palladium layer is formed on a porous support.

CITATION LIST

Non Patent Literature

[Non Patent Literature 1] "HYDROGEN ENERGY SOCIETY" written and edited by Kenji Yamaji, Japan Society of Energy and Resources (2008)

[Non Patent Literature 2] Masaru Ichikawa, "ENGINEERING MATERIALS", 2003, Vol. 51, No. 4, p. 62-69

[Non Patent Literature 3] Okada Yoshimi and others, "HYDROGEN ENERGY SYSTEM", 2006, Vol. 31, No. 2, p. 8-13

[Non Patent Literature 4] Ito Naotsugu and others, "ENGINEERING MATERIALS", 2003, Vol. 51, No. 4, p. 74-76

SUMMARY OF INVENTION

Technical Problem

Conventionally, in the case of making hydrogen present with the organic compound in order to prevent the reduction in activity of the dehydrogenation catalyst in the dehydrogenation reaction of the organic compound, there is no choice but to supply hydrogen from a supply source outside a reaction system to the reaction system. It causes less problem in a hydrogen station equipped with a compressor for hydrogen or a pressure accumulator because it is easy to secure the supply source of hydrogen. However, in the case of conducting the dehydrogenation reaction of the organic compound in a movable body such as fuel cell vehicles or hydrogen engine vehicles which has a difficulty in installing the compressor or the pressure accumulator, it is difficult to secure the supply source of hydrogen for preventing the reduction in activity of the dehydrogenation catalyst.

The present invention has been made in view of the aforementioned problems, and an object of the present invention is to provide a reactor for dehydrogenation of an organic compound, a hydrogen production apparatus, and a hydrogen production process whereby it is possible to suppress a reduction in activity of a dehydrogenation catalyst easily in production of hydrogen using a dehydrogenation reaction of the organic compound.

Solution to Problem

[First Aspect of the Present Invention]

Aiming at achieving the above object, a reactor for dehydrogenation of an organic compound according to a first aspect of the present invention is a flow-type reactor, comprising: a hydrogen separation membrane selectively permeable to hydrogen; and a dehydrogenation catalyst for promoting a dehydrogenation reaction of an organic compound which can release hydrogen upon the dehydrogenation reaction, and including: a reaction side area through which the organic compound can flow and which includes the dehydrogenation catalyst; and a permeation side area which is separated from the reaction side area by the hydrogen separation membrane and through which hydrogen that has passed through the hydrogen separation membrane can flow, the reactor for dehydrogenation of an organic compound including, in this order along a flow direction of the organic compound: a part B in which the hydrogen separation membrane is present and the dehydrogenation catalyst is not present; and a part A in which both of the hydrogen separation membrane and the dehydrogenation catalyst are present.

It is preferred that the dehydrogenation catalyst is not placed upstream of a most upstream edge of the part B along the flow direction of the organic compound.

It is preferred that the organic compound is selected from cyclohexane, methylcyclohexane, decalin, tetralin, 2-propanol, or a mixture thereof.

A hydrogen production process according to the first aspect of the present invention uses the reactor for dehydrogenation of the first aspect of the present invention, wherein a) a step of transferring hydrogen generated by the dehydrogenation reaction of the organic compound in the reaction side area of the part A to the permeation side area through the hydrogen separation membrane and b) a step of transferring hydrogen provided to the permeation side area in the step a to the reaction side area of the part B through the hydrogen separation membrane are conducted concurrently.

[Second Aspect of the Present Invention]

Aiming at achieving the above object, a hydrogen production apparatus according to a second aspect of the present invention comprises a reactant container into which an organic compound which releases hydrogen in the presence of a dehydrogenation catalyst is to be introduced; a flow-type reactor which is connected to the reactant container and contains a dehydrogenation catalyst; a product container which is connected to the reactor and located at the opposite side of the reactant container across the reactor; a hydrogen container which is adjacent to both of the reactant container and the product container; a first hydrogen separation membrane which separates a space in the hydrogen container from a space in the product container; and a second hydrogen separation membrane which separates a space in the hydrogen container from a space in the reactant container. It is noted that the hydrogen separation membrane means a membrane which is selectively permeable to hydrogen in the second aspect of the present invention.

A hydrogen production process according to the second aspect of the present invention is a hydrogen production process using the hydrogen production apparatus according to the second aspect of the present invention, and comprises a first step of supplying the organic compound introduced into the reactant container to the reactor and allowing the organic compound in the reactor to release hydrogen, and supplying hydrogen released in the reactor to the product container and supplying hydrogen in the product container to the hydrogen container through the first hydrogen separation membrane; and a second step of supplying a part of hydrogen supplied to the hydrogen container to the reactant container through the second hydrogen separation membrane, and supplying hydrogen supplied to the reactant container and the organic compound introduced into the reactant container to the reactor, wherein the first step and the second step are conducted concurrently.

In the second aspect of the present invention, a part of hydrogen generated by the dehydrogenation reaction of the organic compound in the reactor is supplied again to the reactor with the organic compound before the dehydrogenation reaction. By this, the dehydrogenation reaction of the organic compound proceeds in the presence of hydrogen in the reactor. As a result, it is possible to suppress a reduction in activity of the dehydrogenation catalyst in the second aspect of the present invention. That is, in the second aspect of the present invention, a part of hydrogen produced in the production apparatus is reused for suppressing deterioration of the dehydrogenation catalyst. Accordingly, in the second aspect of the present invention, there is no need to supply hydrogen to the dehydrogenation catalyst from a supply source of hydrogen outside the apparatus as in the conventional techniques.

In the hydrogen production process according to the second aspect of the present invention, it is preferred that the organic compound is at least one selected from the group consisting of cyclohexane, methylcyclohexane, decalin, tetralin, and 2-propanol. These organic compounds are advantageous in that these organic compounds easily release hydrogen by the dehydrogenation reaction and easily store hydrogen by a hydrogenation reaction after the dehydrogenation reaction. That is, the aforementioned organic compound is easily reused as a medium for transportation and storage of hydrogen.

Advantageous Effects of Invention

According to the first and the second aspects of the present invention, it is possible to provide a reactor for dehydrogenation of an organic compound, a hydrogen production apparatus, and a hydrogen production process whereby it is possible to suppress a reduction in activity of a dehydrogenation catalyst easily in production of hydrogen using a dehydrogenation reaction of the organic compound.

DESCRIPTION OF EMBODIMENTS

[Embodiments of First Aspect of the Present Invention]

Hereinafter, a description will be given of preferred embodiments (a first embodiment and a second embodiment) of a first aspect of the present invention in detail. It should be noted that the first aspect of the present invention is not limited to the following embodiments. It is noted that the same or equal elements are donated by the same reference numerals. Moreover, positional relationship among the left, right, top, and bottom is as shown in Figures, but a dimensional ratio is not limited to those shown in Figures. Furthermore, a pressure value described below is given in absolute pressure.

The first embodiment relates to a technique of generating hydrogen by means of a dehydrogenation reaction of an organic compound. More particularly, the first embodiment relates to a technique in which deterioration in activity of a dehydrogenation catalyst is suppressed by a simple device in the case of generating hydrogen by means of a dehydrogenation reaction of an organic compound. It is noted that, hereinafter, absolute pressure is used in a description about pressure and upstream and downstream are considered along a flow direction of the organic compound (raw material), unless it is explicitly stated otherwise.

When hydrogen is generated by dehydrogenating the organic compound, generally, hydrogen is added to the organic compound in order to prevent deterioration of the dehydrogenation catalyst. In the conventional techniques, there is no choice but to conduct the addition of hydrogen by using hydrogen which has been separately high-pressurized. That is, there is a need to prepare a high-pressure hydrogen source such as a compressed hydrogen tank, This is possible in a hydrogen station, but is difficult for use in a vehicle such as a fuel cell vehicle. According to the first embodiment, it is possible to make a reacting flow which is to be provided to the dehydrogenation reaction contain hydrogen without using a special device, and therefore, a process and a device suitable even for use in a vehicle are provided.

<Organic Compound>

A reactor for dehydrogenation of the first embodiment comprises a dehydrogenation catalyst which promotes the dehydrogenation reaction of the organic compound. The organic compound can release hydrogen by the dehydrogenation reaction. As the organic compound, an organic compound which can release hydrogen by the dehydrogenation reaction to be converted into an unsaturated compound can be used. It is preferred that release of hydrogen is reversible in view of the fact that such organic compound can be reused after subjected to regeneration (hydrogenation). However, release of hydrogen may be irreversible.

As the organic compound, a group of compounds generally referred to as organic hydrides are preferred. The organic hydrides can reversibly release hydrogen by the dehydrogenation reaction to be converted into unsaturated compounds. Examples of the organic hydrides include cyclohexane, methylcyclohexane, tetralin, and decalin, However, even other than those, an organic compound which can release hydrogen by the dehydrogenation reaction to be converted into an unsaturated compound can be preferably used. Partial examples of such a compound include ethanol, 2-propanol, 2-butanol, piperidine, piperazine, hexahydropyrimidine, hexahydro-1,3,5-triazine, decahydroquinoline, and decahydroisoquinoline.

These compounds release hydrogen by the dehydrogenation reaction, and provide unsaturated compounds such as benzene in the case of cyclohexane, toluene in the case of methylcyclohexane, and acetone in the case of 2-propanol.

<Dehydrogenation Catalyst>

A catalyst is used for the dehydrogenation reaction. As the catalyst, though a known arbitrary catalyst which can promote the dehydrogenation reaction of the organic compound can be used, a metal such as Pt, Ni, Ru, Rh, Pd, Ir, and Os or an alloy thereof is preferably used. Moreover, these metals (including the alloy) can be preferably used in a configuration in which these compounds are supported by an appropriate support such as alumina, silica, magnesia, silicaalumina, zeolite, and zirconia, and as needed, can be those in which an appropriate additive such as alkali metal elements, alkali earth metal elements, La, and La series elements is added. Furthermore, there is no limit on a shape of the catalyst, and one having any shape such as a granular shape, a powder shape, and a honeycomb shape can be used.

<Hydrogen Separation Membrane>

In the first embodiment, a hydrogen separation membrane is used with the dehydrogenation catalyst mentioned above. As the hydrogen separation membrane, any which has a function that selectively allows hydrogen to pass therethrough can be arbitrarily used, and for example, a porous ceramics membrane such as a porous alumina membrane, a porous silica membrane, a porous zirconia membrane, a zeolite membrane, a porous glass membrane, and a porous carbon membrane is preferably used. Also, it is possible to use a metal membrane such as a palladium membrane or a palladium alloy membrane such as Pd, Pd—Cu, and Pd—Ag, and a non-precious metal alloy membrane containing a metal such as Ti, Zr, Hf, V, Nb, Ta, Cr, Mo, W, and Ni. In the case of using the non-precious metal alloy membrane, it is possible to form a thin membrane of Pd on a surface of this membrane by a process such as vapor deposition, as needed.

<Reactor for Dehydrogenation>

Figure 1:
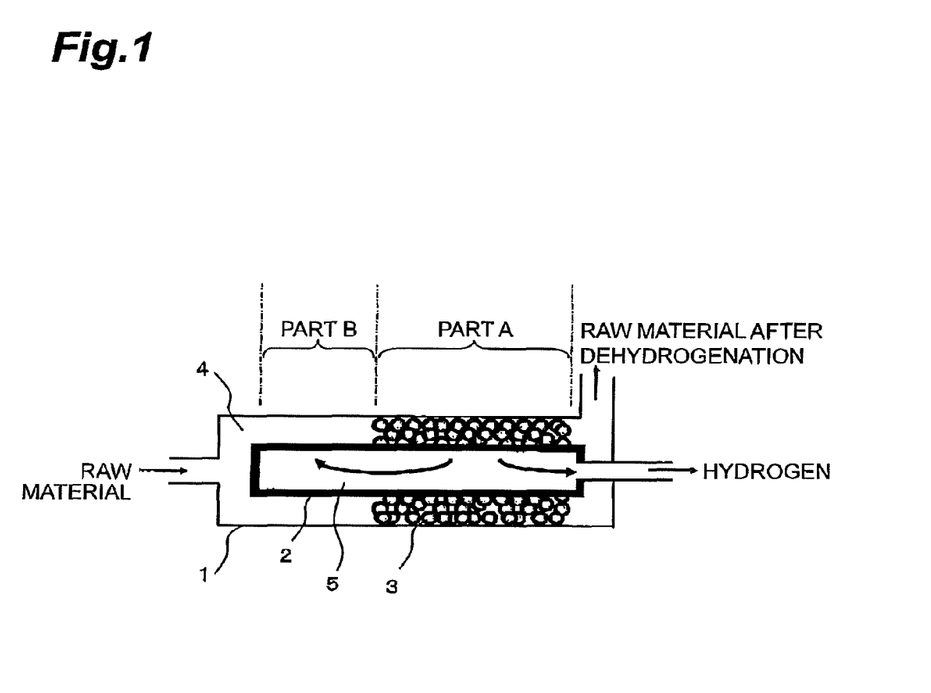
FIG. 1 is a schematic cross-sectional view illustrating one embodiment (a first embodiment) of a reactor for dehydrogenation of a first aspect of the present invention.

FIG. 1 is a cross-sectional view schematically illustrating one embodiment of a reactor for dehydrogenation (hereinafter, it may be referred to as reactor) of the first embodiment of the present invention. The raw material flows from left to right in the Figure. A hydrogen separation membrane 2 is placed in a reaction container 1. It is possible to arbitrarily determine shapes of the reaction container and the hydrogen separation membrane individually. Moreover, it is possible to place one or more hydrogen separation membranes in one reaction container. For example, it is possible to place one or more cylindrical hydrogen separation membranes in a cylindrical-shaped reaction container 1.

The reactor includes a reaction side area 4 in which the organic compound which is the raw material flows, and a permeation side area 5 which is separated from the reaction side area 4 by the hydrogen separation membrane 2 and in which purified hydrogen which has passed through the hydrogen separation membrane 2 flows.

Furthermore, aside from the distinction between the reaction side area and the permeation side area, the reactor includes two distinguished parts: a part A in which both of the hydrogen separation membrane 2 and a dehydrogenation catalyst 3 are present, and a part B in which the hydrogen separation membrane is present and the dehydrogenation catalyst is not present. The part A is located downstream of the part B along a flow direction of the raw material. The reaction side area of the part B and the reaction side area of the part A are communicated with each other, and the permeation side area of the part B and the permeation side area of the part A are communicated with each other.

In the part B which is located upstream between the part B and the part A, the hydrogen separation membrane is placed but the dehydrogenation catalyst is not placed. The reaction side area includes the dehydrogenation catalyst 3.

In this embodiment, both of the part A and the part B are composed of the continuous reaction container and the continuous hydrogen separation membrane, and the part A and the part B are distinguished by the presence or absence of the dehydrogenation catalyst along the flow direction of the raw material.

Figure 2:
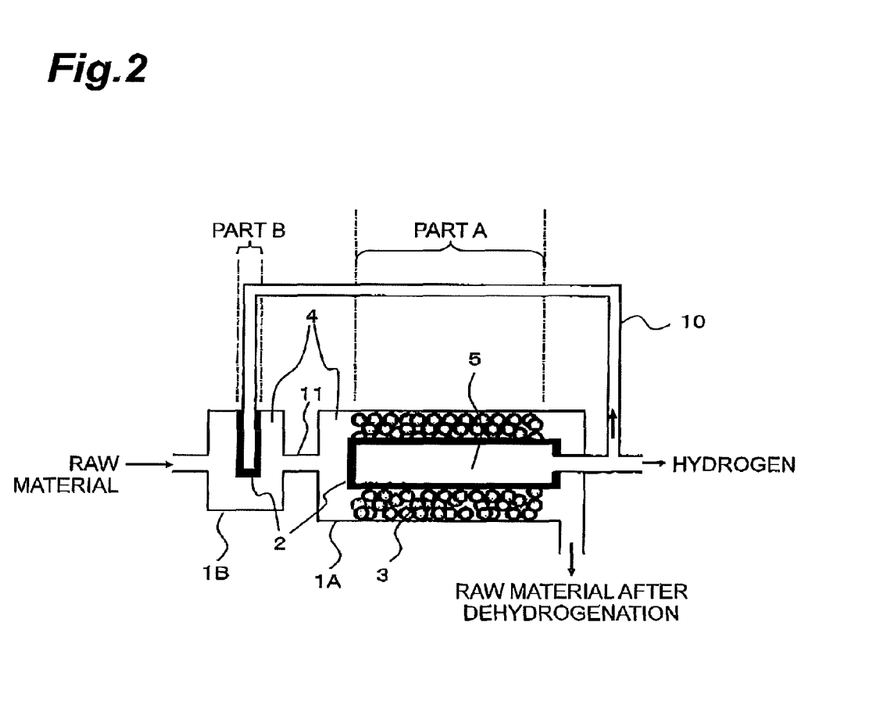
FIG. 2 is a schematic cross-sectional view illustrating another embodiment (a second embodiment) of a reactor for dehydrogenation of the first aspect of the present invention.

Another embodiment (second embodiment) of the reactor for dehydrogenation is illustrated in FIG. 2. In this embodiment, the part A and the part B are formed separately as reaction containers 1a and 1b. The reaction side area of the part B and the reaction side area of the part A are communicated with each other through a pipe 11. A pipe 10 for supplying hydrogen provided to the permeation side area 5 of the hydrogen separation membrane to the part B via outside of the reaction container is installed. Hydrogen provided to the permeation side area 5 goes through the pipe 10, and passes through the hydrogen separation membrane 2 of the part B to be supplied to the reaction side area of the part B. This embodiment is one in which the part A and the part B are separated.

It is not necessary that the whole of a wall which separates the reaction side area and the permeation side area is formed of the hydrogen separation membrane. In the first embodiment, the hydrogen separation membrane is used for allowing hydrogen generated in the dehydrogenation catalyst layer 3 (the reaction side area of the part A) to pass therethrough into the permeation side area 5 and for allowing hydrogen in the permeation side area to flow backward into the reaction side area of the part B. In view of this point, it is possible to determine which part of the wall separating the reaction side area and the permeation side area is formed of the hydrogen separation membrane.

In view of more readily preventing all of the dehydrogenation catalysts included in the reactor for dehydrogenation from deactivation or coking, it is desirable not to place the dehydrogenation catalyst upstream of a most upstream edge of the part B along the flow direction of the raw material in the reactor for dehydrogenation. On the other hand, the part A in which both of the hydrogen separation membrane and the dehydrogenation catalyst are present is placed downstream of the part B, and it is also appropriate to place a part in which the hydrogen separation membrane is present and the dehydrogenation catalyst is not present (a part B placed in addition to the part B illustrated in Figure) or a part in which the dehydrogenation catalyst is present but the hydrogen separation membrane is not present, downstream of the part B aside from the part A.

The part B may be placed at a plurality of places and the part A may be placed at a plurality of places. In any cases, it is preferred that the dehydrogenation catalyst is not placed upstream of an upstream edge of the part B. That is, it is preferred that the dehydrogenation catalyst is not present, accordingly the part A is not present, upstream of the part B in the case in which the part B is present in a singular number, or upstream of the part. B which is located most upstream in the case in which the part B is present in a plurality of numbers.

For flow control of gas and the like, the reactor for dehydrogenation can arbitrarily include a part in which the hydrogen separation membrane and the dehydrogenation catalyst are not present.

In the part B in which the dehydrogenation catalyst is not placed, it is possible to pack a filler not having activity of the dehydrogenation catalyst, such as quartz, silica, and alumina, or to install a structure made of a material having no effect on the reaction such as stainless steel, for the purpose of securing mechanical strength or the like, as needed.

In the reaction side area 4 of the part A, hydrogen is generated by the dehydrogenation catalyst and at least a part thereof passes through the hydrogen separation membrane 2. The permeation side area 5 of the hydrogen separation membrane is set to have an appropriate pressure (hereinafter, referred to as permeation side pressure) and filled with high-purity hydrogen. On the other hand, in the reaction side area 4 of the part B, a partial pressure of hydrogen is low because the dehydrogenation catalyst is not present and the organic compound which is a fresh raw material flows in continuously. However, inside the hydrogen separation membrane (permeation side area) of this part, hydrogen under the permeation side pressure is present, and therefore, in the part B, there arises a situation in which the partial pressure of hydrogen in the permeation side area is higher than the partial pressure of hydrogen in the reaction side area. Therefore, by the difference in the partial pressure of hydrogen, hydrogen is transferred from the permeation side area to the reaction side area in the part B, thereby hydrogen is supplied to the reaction side area.

The hydrogen separation membrane can be divided into a part included in the part A and a part included in the part B. The ratio is generally, in terms of a ratio between an area of the hydrogen separation membrane included in the part A, SA, and an area of the hydrogen separation membrane included in the part B, SB, (SA:SB), preferably 1:99 to 99:1, more preferably 5:95 to 95:5, still more preferably 10:90 to 90:10. When the ratio is 1:99 or more, it is possible to allow the amount of hydrogen provided to reaction side area through the hydrogen separation membrane to be a preferable amount, and on the other hand, the ratio is 99:1 or less, it is possible to allow the amount of hydrogen generated by the dehydrogenation reaction and transferred to the permeation side to be a preferable amount.

A description will be given of operation conditions of the reactor for dehydrogenation mentioned above. As for a temperature, while it is possible to control the part A and the part B independently, or control the part A and the part B together, in either case, the range of the temperature is preferably from 50° C. to 500° C., more preferably from 100° C. to 450° C., still more preferably from 150° C. to 400° C. It is noted that the temperature here means a temperature in the reaction side area, and it is possible to monitor the temperature by inserting a thermocouple at an appropriate position of the reaction side area as needed.

As for a pressure, a pressure in the reaction side area ranges from preferably 0.1 MPa to 10 MPa, more preferably 0.2 MPa to 5 MPa, still more preferably 0.3 MPa to 2 MPa. When the reaction side pressure is 0.1 MPa or more, it is easy to ensure the differential pressure with the permeation side pressure and it is possible to exert performance of the hydrogen separation membrane easily. On the other hand, in view of inhibiting breaking of the hydrogen separation membrane, the pressure is preferably 10 MPa or less.

Next, a description will be given of a pressure of the permeation side area. Generally, a pressure lower than the pressure of the reaction side area is employed, and a pressure preferably of 0.01 MPa to 2 MPa, more preferably of 0.05 MPa to 1 MPa, still more preferably of ordinary pressure (atmospheric pressure) to 0.6 MPa is employed. When the pressure is 0.01 MPa or more, a preferable amount of hydrogen is transferred to the reaction side, and it is possible to achieve an effect of suppressing deterioration of the dehydrogenation catalyst easily. On the other hand, when the pressure is 2 MPa or less, it is easy to transfer a preferable amount of hydrogen from the reaction side area to the permeation side area.

A supplied amount of the organic compound to the dehydrogenation catalyst is preferably 0.1 to1000 (mmol/catalyst g·h), more preferably 0.5 to 500 (mmol/catalyst g·h), still more preferably 1 to 100 (mmol/catalyst g·h), in terms of millimole number per 1 g of the dehydrogenation catalyst and per hour. When this value is 0.1 or more, it is possible to prevent a reduction in productivity easily, and the value is 1000 or less, it is easy to attain a preferable conversion rate and a preferable hydrogen yield.

In the reactor for dehydrogenation, it is possible to arbitrarily install a raw material introducing inlet or a raw material introducing pipe, a hydrogen separation membrane outlet or a hydrogen discharging pipe, and a reaction side outlet or a raw material discharging pipe after dehydrogenation.

By using the dehydrogenation device according to the first and the second embodiments, it is easy to concurrently conduct a) a step of transferring hydrogen generated by the dehydrogenation reaction of the organic compound in the reaction side area of the part A to the permeation side area through the hydrogen separation membrane and b) a step of transferring hydrogen provided to the permeation side area in the step a to the reaction side area of the part B through the hydrogen separation membrane.

By the step b, hydrogen is supplied to the reaction side area of the part B, that is, hydrogen is added to the raw material upstream of the dehydrogenation catalyst, thereby deterioration of the dehydrogenation catalyst is suppressed.

According to the first and the second embodiments, it is possible to realize reaction conditions whereby deterioration of the dehydrogenation catalyst is suppressed by a simple device. However, one thing which should be pointed out is that, in some cases, the yield of hydrogen is slightly decreased in comparison with the case where the same amount of catalyst is used and backward flow is not conducted because a part of hydrogen which should become product hydrogen directly is allowed to flow backward into the reaction side area. However, this shortcoming can be sufficiently compensated for by the effect of suppressing deterioration of the dehydrogenation catalyst.

According to the first and the second embodiments, the difference in the partial pressure of hydrogen is used for supplying hydrogen obtained in the permeation side area of the part A to the reaction side area of the part B located upstream of the part A, that is, for returning hydrogen upstream of the dehydrogenation catalyst layer, and a booster means is not required. That is, it is possible to supply hydrogen for deterioration of the catalyst to the catalyst layer extremely easily and simply.

[Embodiments of Second Aspect of the Present Invention]

Hereinafter, a description will be given of preferred embodiments (a third embodiment and a fourth embodiment) of a second aspect of the present invention in detail. It should be noted that the second aspect of the present invention is not limited to the following embodiments. It is noted that the same or equal elements are donated by the same reference numerals. Moreover, positional relationship among the left, right, top, and bottom is as shown in Figures, but a dimensional ratio is not limited to those shown in Figures. Furthermore, a pressure value described below is given in absolute pressure.

(Third Embodiment)

Hereinafter, a description will be given of a hydrogen production apparatus according to an embodiment (the third embodiment) of the second aspect of the present invention and a hydrogen production process using the production apparatus, with reference to FIG. 5.

<Summary of Production Apparatus>

A hydrogen production apparatus 2A comprises a reactant container 44, a flow-type reactor 48, a product container 40, and a hydrogen container 42. The reactor 48 is connected to the reactant container 44 via a pipe 30. The product container 40 is connected to the reactor 48 via a pipe 32. The reactor 48 is located between the reactant container 44 and the product container 40. An organic compound (reactant) which releases hydrogen in the presence of a dehydrogenation catalyst is introduced into the reactant container 44. The reactor 48 includes a dehydrogenation catalyst 3. The dehydrogenation catalyst 3 is not present in the reactant container 44 and the product container 40. The hydrogen container 42 is composed of an upstream side hydrogen container 14, a downstream side hydrogen container 18, and a connecting pipe 16 which connects the upstream side hydrogen container 14 and the downstream side hydrogen container 18. It is noted that "upstream side" means the side in which the reactant container 44 is located with respect to the reactor 48, in the third embodiment. "Downstream side" means the side in which the product container 40 is located with respect to the reactor 48. Hereinafter, the reactant container 44, the reactor 48, and the product container 40 are described as "reaction system" in some cases.

The downstream side hydrogen container 18 which is a part of the hydrogen container 42 is adjacent to the product container 40. An internal space of the downstream side hydrogen container 18 and an internal space of the product container 40 are separated by a plate-shaped first hydrogen separation membrane 20A. The upstream side hydrogen container 14 which is a part of the hydrogen container 42 is adjacent to the reactant container 44. An internal space of the upstream side hydrogen container 14 and an internal space of the reactant container 44 are separated by a plate-shaped second hydrogen separation membrane 20B. Hereinafter, "the first hydrogen separation membrane" is described as "the first membrane" in some cases. Also, "the second hydrogen separation membrane" is described as "the second membrane" in some cases.

The hydrogen production apparatus 2A includes a part in which the hydrogen separation membrane and the dehydrogenation catalyst are not present for flow control of the organic compound and hydrogen. For the purpose of providing mechanical strength to the reactant container 44 and the product container 40 in which the dehydrogenation catalyst 3 is not present, a filler made of a material not having activity of the dehydrogenation catalyst such as quartz, silica, and alumina may be packed in the reactant container 44 and the product container 40. Moreover, a structure or the like made of a material having no effect on the dehydrogenation reaction such as stainless steel or the like may be installed in the reactant container 44 and the product container 40 to provide mechanical strength to each container. Furthermore, measures of providing mechanical strength by the filler or the structure can be employed in the upstream side hydrogen container 14, the downstream side hydrogen container 18, or the whole hydrogen container 42.

<Organic Compound>

As the organic compound which is the raw material of hydrogen, an organic compound which releases hydrogen by the dehydrogenation reaction is used. For example, an organic compound which releases hydrogen by the dehydrogenation reaction to be converted into an unsaturated compound may be used. This unsaturated compound can be reused as a medium for transportation and storage of hydrogen by being subjected to hydrogenation. Therefore, an organic compound which releases hydrogen reversibly is preferred. It is noted that an organic compound which releases hydrogen irreversibly may be used.

As the organic compound reversibly releasing hydrogen, organic hydrides are preferred. The organic hydrides release hydrogen by the dehydrogenation reaction to be converted into unsaturated compounds, and then, store hydrogen by the hydrogenation reaction. Examples of the organic hydrides include cyclohexane, methylcyclohexane, tetralin, and decalin. Instead of the organic hydrides, ethanol, 2-propanol, 2-butanol, piperidine, piperazine, hexahydropyrimidine, hexahydro-1,3,5-triazine, decahydroquinolinel, decahydroisoquinoline, or the like may be used. These organic compounds also release hydrogen by the dehydrogenation reaction to be converted into unsaturated compounds. For example, cyclohexane is converted into benzene by the dehydrogenation reaction. Methylcyclohexane is converted into toluene by the dehydrogenation reaction. 2-propanol is converted into acetone by the dehydrogenation reaction. It is noted that the aforementioned organic compounds can be used alone or in combination of a plurality thereof.

<Dehydrogenation Catalyst>

As the dehydrogenation catalyst 3 which promotes the dehydrogenation reaction of the organic compound, a metal such as Pt, Ni, Ru, Rh, Pd, Ir, and Os or an alloy thereof is preferred. Moreover, the metal or the alloy supported by a support such as alumina, silica, magnesia, silicaalumina, zeolite, and zirconia may be used as the dehydrogenation catalyst 3. An additive such as alkali metal elements, alkali earth metal elements, and La series elements may be added to the dehydrogenation catalyst 3 as needed. There is no limit on a shape of the dehydrogenation catalyst 3, and any shape such as a granular shape, a powder shape, and a honeycomb shape can be employed. The reactor 48 may include only one of the aforementioned dehydrogenation catalysts or a plurality of the dehydrogenation catalysts.

<Hydrogen Separation Membrane>

As the first hydrogen separation membrane 20A and the second hydrogen separation membrane 20B, a membrane which has a function that selectively allows hydrogen to pass therethrough may be used, As the first membrane 20A and the second membrane 20B, for example, a porous ceramics membrane such as a porous alumina membrane, a porous silica membrane, a porous zirconia membrane, a zeolite membrane, a porous glass membrane, and a porous carbon membrane is preferred. Also, it is possible to use a metal membrane such as a Pd membrane, a palladium alloy membrane such as Pd—Cu and Pd—Ag, and a alloy membrane containing a non-precious metal such as Ti, Zr, Hf, V, Nb, Ta, Cr, Mo, W, and Ni as the first membrane 20A and the second membrane 20B. In the case of using the non-precious metal alloy membrane, a thin membrane of Pd may be formed on a surface of the non-precious metal alloy membrane by a process such as vapor deposition, as needed.

<Hydrogen Production Process>

In a hydrogen production process according to the third embodiment, a first step and a second step described below are conducted concurrently by using the hydrogen production apparatus 2A illustrated in FIG. 5.

Temperatures of the reactant container 44, the reactor 48, and the product container 40 in the first step and the second step are preferably 50 to 500° C., more preferably 100 to 450° C., most preferably 150 to 400° C. By this, the dehydrogenation reaction of the organic compound is promoted. It is noted that it is possible to monitor the temperatures of the reactant container 44, the reactor 48, and the product container 40 each by thermocouples inserted in the each part. The temperatures of the reactant container 44, the reactor 48, and the product container 40 may be controlled independently or together. Hereinafter, as an example of the hydrogen production process, a case in which gas of the organic compound is introduced into the reactant container 44 will be described.

[First Step]

In the first step, gas of the organic compound is introduced continuously into the reactant container 44 through an introducing pipe 22 installed in the reactant container 44. The organic compound does not pass through the second membrane 20B, and flows from the reactant container 44 into the reactor 48. In the reactor 48, the dehydrogenation reaction of the organic compound is promoted by the dehydrogenation catalyst 3, and the organic compound releases hydrogen gas and at the same time is converted into an unsaturated compound. The hydrogen gas and the unsaturated compound generated in the reactor 48 flow into the product container 40.

A supplied amount of the organic compound to the dehydrogenation catalyst 3 is preferably 0.1 to 1000 (mmol/g·hour), more preferably 0.5 to 500 (mmol/g·hour), most preferably 1 to 100 (mmol/g·hour), with respect to a mass of the dehydrogenation catalyst. When the value is 0.1 or more, it is possible to suppress a reduction in productivity of hydrogen easily. When the value is 1000 or less, a conversion rate of the organic compound (yield of hydrogen) is easily improved. It is noted that the unit of the supplied amount of the organic compound, "mmol/g·hour" means millimole number of the organic compound which is supplied to 1 g of the dehydrogenation catalyst per hour.

Since a partial pressure of the hydrogen gas in the downstream side hydrogen container 18 is lower than a partial pressure of the hydrogen gas in the product container 40, the hydrogen gas in the product container 40 passes through the first membrane 20A to be transferred into the downstream side hydrogen container 18 by the differential pressure of the hydrogen gas. The hydrogen gas in the downstream side hydrogen container 18 is recovered through a hydrogen discharging pipe 26 installed in the downstream side hydrogen container 18. The unsaturated compound (organic compound after dehydrogenation) in the product container 40 does not pass through the first membrane 20A, and is recovered through an organic compound discharging pipe 24 installed in the product container 40.

[Second Step]

A part of the hydrogen gas transferred from the product container 40 into the downstream side hydrogen container 18 in the first step flows into the upstream side hydrogen container 14 via the connecting pipe 16. Therefore, the upstream side hydrogen container 14 is filled with high-purity hydrogen gas. On the other hand, the reactant container 44 is filled with the gas of flesh organic compound before dehydrogenation. Since the dehydrogenation catalyst is not present in the reactant container 44, the dehydrogenation reaction of the organic compound does not proceed in the reactant container 44. Therefore, the partial pressure of the hydrogen gas in the upstream side hydrogen container 14 is higher than the partial pressure of the hydrogen gas in the reactant container 44. By this differential pressure of the hydrogen gas, the hydrogen gas in the upstream side hydrogen container 14 passes through the second membrane 20B to be transferred into the reactant container 44. The hydrogen gas transferred into the reactant container 44 and the organic compound introduced into the reactant container 44 are allowed to flow into the reactor 48. As a result, in the reactor 4, the dehydrogenation reaction of the organic compound proceeds as in the case in the first step. Moreover, in the second step, the hydrogen gas suppresses coking (precipitation of carbon on a surface of the dehydrogenation catalyst 3) in the reactor 4, thereby deactivation of the dehydrogenation catalyst 3 is suppressed.

Internal pressures in the reactant container 44, the reactor 48, and the product container 40 in the first step and the second step (hereinafter, described as "reaction system pressure") are preferably 0.1 M to 10 MPa, more preferably 0.2 M to 5 MPa, preferably 0.3 M to 2 MPa.

When the reaction system pressure is 0.1 MPa or more, it becomes easy to ensure the differential pressure between the reaction system pressure and an internal pressure of the downstream side hydrogen container 18 and exert a function of the first membrane 20A that allows hydrogen to pass therethrough. On the other hand, when the reaction system pressure is 10 MPa or less, it becomes easy to inhibit breaking of the first membrane 20A and the second membrane 20B.

An internal pressure of the hydrogen container 42 (that is, internal pressures of the upstream side hydrogen container 14, the connecting pipe 16, and the downstream side hydrogen container 18) in the first step and the second step is controlled to a value lower than the reaction system pressure. The internal pressure of the hydrogen container 42 is preferably 0.01 M to 2 MPa, more preferably 0.05 M to 1 MPa, most preferably ordinary pressure (atmospheric pressure) to 0.6 MPa.

When the internal pressure of the upstream side hydrogen container 14 is 0.01 MPa or more, a preferable amount of hydrogen passes through the second membrane 20B to be transferred from the upstream side hydrogen container 14 into the reactant container 44, and it becomes easy to suppress deterioration of the dehydrogenation catalyst 3, On the other hand, when the internal pressure of the downstream side hydrogen container 18 is 2 MPa or less, a preferable amount of hydrogen easily passes through the first membrane 20A to be transferred from the product container 40 into the downstream side hydrogen container 18.

The reaction system pressure and the internal pressure of the hydrogen container 42 may be controlled by the temperatures of the reactant container 44, the reactor 48, and the product container 40, a supply rate of the organic compound to the reactant container 44, deaeration from the organic compound discharging pipe 24 and the hydrogen discharging pipe 26, or the like. The reaction system pressure may be measured by a pressure meter 28A installed in the pipe 30 which connects the reactant container 44 and the reactor 48. The internal pressure of the hydrogen container 42 may be measured by a pressure meter 28B installed in the hydrogen discharging pipe 26 of the downstream side hydrogen container 18.

A ratio between an area of the second hydrogen separation membrane 20B, S2, and an area of the first hydrogen separation membrane, S1, (S2/S1), is preferably 1/99 to 99/1, more preferably 5/95 to 95/5, most preferably 10/90 to 90/10. When S2/S1 is 1/99 or more, it is easy to control an amount of hydrogen supplied from the upstream side hydrogen container 14 to the reactant container 44 through the second hydrogen separation membrane 20B to a preferable amount. On the other hand, when S2/S1 is 99/1 or less, it is possible to control an amount of hydrogen transferred from the product container 40 into the downstream side hydrogen container 18 through the first hydrogen separation membrane 20A to a preferable amount.

In the third embodiment, by continuously conducting the first step and the second step concurrently, it is possible to produce hydrogen continuously with suppressing deterioration of the dehydrogenation catalyst 3 by hydrogen added to the raw material (organic compound) at an upstream side of the dehydrogenation catalyst 3.

In the conventional hydrogen production apparatus using the dehydrogenation reaction of the organic compound, there is no choice but to use hydrogen which has been separately high-pressurized outside the apparatus as hydrogen to be added to the organic compound for prevention of deterioration of the dehydrogenation catalyst. That is, conventionally, there is a need to prepare a high-pressure hydrogen source such as a compressed hydrogen tank aside from the hydrogen production apparatus. It is easy to use the high-pressure hydrogen source in a hydrogen station. However, it is technologically and economically difficult to install the high-pressure hydrogen source in a fuel cell vehicle or the like. Therefore, it is difficult to install the conventional hydrogen production apparatus using the dehydrogenation reaction of the organic compound in a vehicle. On the other hand, in the third embodiment, a part of hydrogen obtained by the dehydrogenation reaction of the organic compound proceeding in the apparatus is refluxed, and the hydrogen is added to the organic compound before supplied to the reactor. Accordingly, the hydrogen production apparatus 2A of the third embodiment can be installed alone in a vehicle because it does not require a special high-pressure hydrogen source.

As mentioned above, according to the third embodiment, it is possible to suppress deterioration of the dehydrogenation catalyst by a simple apparatus. However, in some cases, the yield of hydrogen is slightly decreased in comparison with the case where reflux of hydrogen is not conducted because a part of hydrogen which should be recovered as a product is refluxed into the reactant container in the third embodiment. However, a decrease in the yield of hydrogen resulting from reflux of hydrogen can be sufficiently compensated for by an increase in the yield of hydrogen resulting from suppression of deterioration of the dehydrogenation catalyst.

In the third embodiment, reflux of the hydrogen gas from the downstream side hydrogen container 18 to the reactant container 44 located upstream of the downstream side hydrogen container 18 is carried out by the difference in the partial pressure of hydrogen in the apparatus, as mentioned above. That is, in the second step, the difference in the partial pressure of hydrogen is used for refluxing hydrogen from a downstream side of the dehydrogenation catalyst 3 to an upstream side of the dehydrogenation catalyst 3. Therefore, the hydrogen production apparatus 2A according to the third embodiment does not need a mechanical booster means for reflux of hydrogen. That is, in the third embodiment, it is possible to supply hydrogen for suppressing deterioration of the catalyst to the dehydrogenation catalyst 3 extremely easily and simply.

According to the third embodiment, even in the case where the hydrogen separation membrane and the dehydrogenation catalyst are placed at separate parts, it is possible to suppress a reduction in activity of the dehydrogenation catalyst. In the device in which both of the hydrogen separation membrane and the dehydrogenation catalyst are present in the reactor, the dehydrogenation reaction proceeds with shifting equilibrium, and therefore, improvement in the hydrogen yield can be expected but there is a disadvantage that a structure of the reactor becomes complex. On the other hand, according to the way of the apparatus according to the third embodiment in which the hydrogen separation membrane and the dehydrogenation catalyst are placed separately, the structure of the reactor can be simplified. Therefore, the apparatus of the third embodiment is easily downsized with a low cost and is easily put to practical use in the field of fuel cell vehicles or the like.

(Fourth Embodiment)

Figure 6:
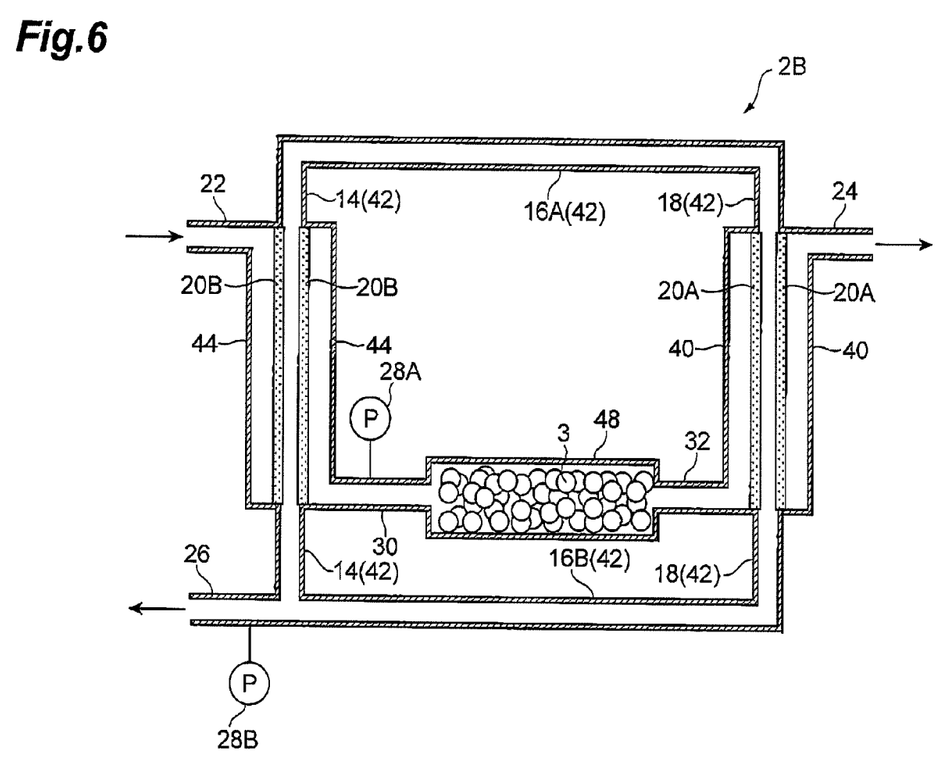
FIG. 6 is a schematic view illustrating a cross section of a hydrogen production apparatus according to a fourth embodiment of the second aspect of the present invention.

Hereinafter, a description will be given of a hydrogen production apparatus and a hydrogen production process according to the fourth embodiment with reference to FIG. 6. A description of common points between the third embodiment and the fourth embodiment will be omitted, and only differences between the two will be described.

A hydrogen container 42 included in a hydrogen production apparatus 213 according to the fourth embodiment is composed of an upstream side hydrogen container 14, a downstream side hydrogen container 18, a first connecting pipe 16A, and a second connecting pipe 16B. The first connecting pipe 16A connects upper ends of the upstream side hydrogen container 14 and the downstream side hydrogen container 18 to each other, and the second connecting pipe 1613 connects lower ends of the upstream side hydrogen container 14 and the downstream side hydrogen container 18 to each other. The first connecting pipe 16A or the second connecting pipe 16B in the fourth embodiment has the same function as that of the connecting pipe 16 in the third embodiment illustrated in FIG. 5.

The hydrogen production apparatus 2B according to the fourth embodiment comprises a cylindrical-shaped reactant container 44. The tube-shaped upstream side hydrogen container 14 (hydrogen container 42) penetrates the reactant container 44 along a central axis of the reactant container 44. In the upstream side hydrogen container 14, a part located at an internal of the reactant container 44 is composed of a cylindrical-shaped second hydrogen separation membrane 20B.

The hydrogen production apparatus 2B according to the fourth embodiment comprises a cylindrical-shaped product container 40. The tube-shaped downstream side hydrogen container 18 (hydrogen container 42) penetrates the product container 40 along a central axis of the product container 40. In the downstream side hydrogen container 18, a part located at an internal of the product container 40 is composed of a cylindrical-shaped first hydrogen separation membrane 20A.

In the aforementioned fourth embodiment, the same function and effect as those in the third embodiment are realized.

Thus, preferred embodiments of the hydrogen production apparatus and the production process according to the second aspect of the present invention have been described, but the second aspect of the present invention is not necessarily limited to the aforementioned embodiments. For example, while a plate-shaped hydrogen separation membrane is used in the third embodiment and a cylindrical-shaped hydrogen separation membrane is used in the fourth embodiment, the shape of the hydrogen separation membrane is not essential one and it is possible to apply a cylindrical-shaped hydrogen separation membrane in the third embodiment and a plate-shaped hydrogen separation membrane in the fourth embodiment. It is possible to arbitrarily select the shape of the hydrogen separation membrane in consideration of a layout of the whole hydrogen production apparatus according to the second aspect of the present invention, the cost, energy efficiency, controllability, and the like comprehensively.

The hydrogen production apparatus may comprise a plurality of reactors between the reactant container and the product container. In the hydrogen production apparatus, a unit composed of the reactant container and the product container sandwiching the reactor therebetween may be installed in a plurality of numbers. In order to prevent deactivation or coking of all of the dehydrogenation catalysts included in the production apparatus, it is desirable not to place the dehydrogenation catalyst at an upstream side of the reactant container which is located at the most upstream side in the production apparatus.

The hydrogen separation membrane may be placed at a plurality of locations in the hydrogen production apparatus. The whole of a separate wall between the reactant container and the upstream side hydrogen container is not necessarily composed of the second hydrogen separation membrane. It is only necessary that at least a part of the separate wall is composed of the second hydrogen separation membrane. The whole of a separate wall between the product container and the downstream side hydrogen container is not necessarily composed of the first hydrogen separation membrane. It is only necessary that at least a part of the separate wall is composed of the first hydrogen separation membrane.

Instead of the introducing pipe 22 for the organic compound, an introducing inlet for the organic compound may be formed in the reactant container 44. The introducing pipe 22 or the introducing inlet for the organic compound may be installed in the reactant container 44 in a plurality of numbers.

Instead of the discharging pipe 24 for the organic compound, a discharging outlet for the organic compound may be formed in the product container 40. The discharging pipe 24 or the discharging outlet for the organic compound may be installed in the product container 40 in a plurality of numbers.

Instead of the hydrogen discharging pipe 26, a discharging outlet for hydrogen may be formed in the downstream side hydrogen container 18. The discharging pipe 26 or the discharging outlet for hydrogen may be installed in the downstream side hydrogen container 18 in a plurality of numbers.

EXAMPLES

[Examples of the First Aspect of the Present Invention]

Hereinafter, the first aspect of the present invention will be described in more detail by Examples 1 and 2, but the first aspect of the present invention is not limited to those Examples.

Example 1

Figure 3:
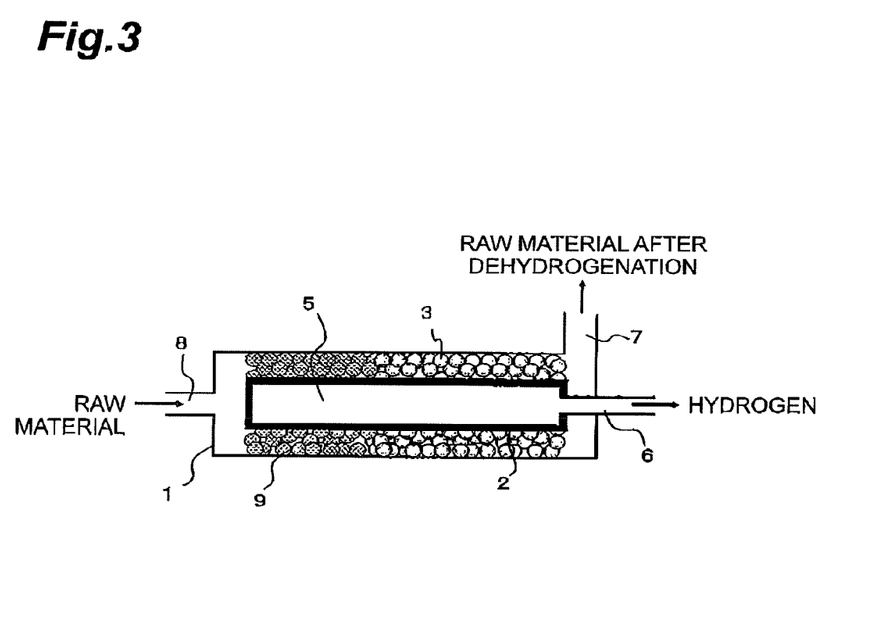
FIG. 3 is a schematic cross-sectional view illustrating a reactor for dehydrogenation used in Example of the first aspect of the present invention.

In FIG. 3, a schematic cross-section of a reactor for dehydrogenation used in this Example is illustrated. A reaction pipe prepared by inserting a cylindrical-shaped hydrogen separation membrane 2 made of a Pd—Ag alloy having an outer diameter of 10 mm (thickness of the alloy membrane 20 μm) into a stainless cylinder having an inner diameter of 25 mm (reaction container 1) was prepared. This hydrogen separation membrane is one produced by precipitating a Pd—Ag alloy membrane on an outer surface of a cylindrical-shaped porous alumina formed body by non-electrolytic plating, and the length of the alloy membrane is 120 mm. Moreover, for preventing leakage, a part of the surface of the porous alumina formed body not including the alloy membrane was sealed with a glass membrane, as needed (not illustrated in FIG. 3).

In the space sandwiched between the stainless cylinder 1 and the hydrogen separation membrane 2 made of a Pd—Ag alloy, quartz balls having an average particle diameter of 1 mm were packed in a region of 40 mm located upstream (reaction side area of the part B), and an alumina-supported 2 mass % platinum catalyst having a bulk density of 0.8 and a particle diameter of 1 to 2 mm was packed in a region of 80 mm located downstream (reaction side area of the part A) to form a catalyst layer 3. A thermocouple, which is not illustrated in FIG. 3, was installed around an outlet of the reaction area side of the part A, and the temperature shown by this was taken as a reaction temperature.

Liquid methylcyclohexane was supplied from an introducing inlet 8 for raw material of the reactor at a rate of 33.0 mL/h. At this time, a sufficient space was provided in the introducing inlet 8 and the temperature was maintained at 200° C. or more so that the entire methylcyclohexane was gasified before entering the catalyst layer. The gasified raw material was introduced into the catalyst layer, and a test was performed by keeping the reaction temperature to 330° C., the pressure in the catalyst layer 3 to 1 MPa, and the pressure of a permeation side area 5 of the hydrogen separation membrane to 0.1 MPa. After 1 hour from the beginning of the test, a product was measured, At first, an analysis conducted at an hydrogen separation membrane outlet 6 revealed that hydrogen having a purity of 99.9 mole % or more was obtained at a rate of 11.0 L/h (at 0° C., 1 atm (0.10 MPa). The same shall apply hereinafter). Moreover, an analysis conducted at a reaction side outlet 7 revealed that the conversion rate of methylcyclohexane was 78%.

The reaction was further continued, and after 100 hours and after 300 hours, the same analysis was conducted. As a result, hydrogen having a purity of 99.9 mole % or more was obtained at 10.3 L/h after 100 hours and at 10.0 L/h after 300 hours at the hydrogen separation membrane outlet 6. Moreover, an analysis conducted at the reaction side outlet 7 revealed that the conversion rate of methylcyclohexane was 75% and 73%, respectively.

Comparative Example 1

Figure 4:
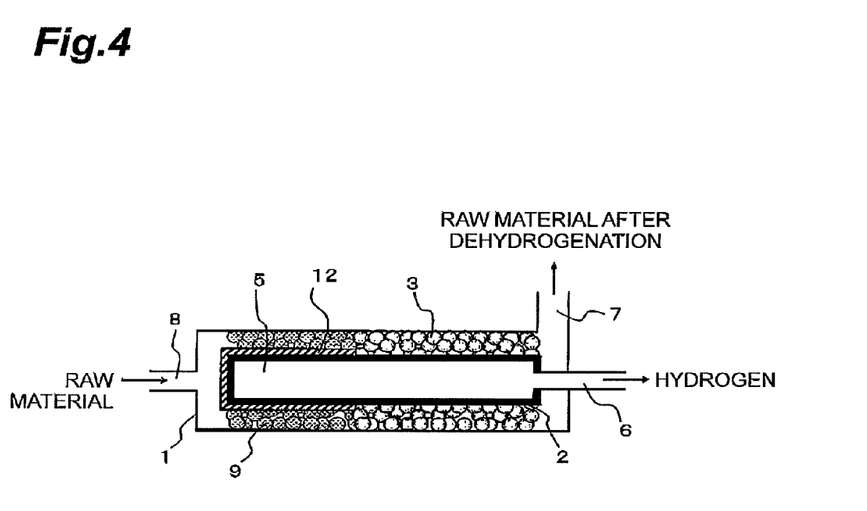
FIG. 4 is a schematic cross-sectional view illustrating a reactor for dehydrogenation used in Comparative Example.

As illustrated in FIG. 4, the part B of the hydrogen separation membrane was provided with glass coating 12 to be inactivated. That is, in this example, the hydrogen separation membrane was not present in a part corresponding to the part B in Example 1. Except that, the same test as that in Example 1 was performed.

At first, an analysis conducted at the hydrogen separation membrane outlet 6 after 1 hour from the beginning of the test revealed that hydrogen having a purity of 99.9 mole % or more was obtained at a rate of 11.7 L/h. Moreover, an analysis conducted at the reaction side outlet 7 revealed that the conversion rate of methylcyclohexane was 80%.

The reaction was further continued, and the same analysis was conducted after 100 hours and 300 hours. As a result, hydrogen having a purity of 99.9 mole % or more was obtained at the hydrogen separation membrane outlet 6 but the amount was reduced to 8.0 L/h after 100 hours and further to 4.3 L/h after 300 hours. Moreover, an analysis conducted at the reaction side outlet 7 revealed that the conversion rate of methylcyclohexane was 56% and 32%, respectively.

As just described, in the case where the present invention is not used, it was found that the initial hydrogen yield was high but activity of the catalyst rapidly decreased.

Example 2

The same test as that in Example 1 was performed except that cyclohexane was used instead of methylcyclohexane.

As a result, an analysis conducted at first at the hydrogen separation membrane outlet 6 revealed that hydrogen having a purity of 99.9 mole % or more was obtained at a rate of 12.6 L/h. Moreover, an analysis conducted at the reaction side outlet 7 revealed that the conversion rate of cyclohexane was 74%.

The reaction was further continued, and the same analysis was conducted after 100 hours and 300 hours. As a result, hydrogen having a purity of 99.9 mole % or more was obtained at 12.1 L/h after 100 hours and at 11.8 L/h after 300 hours at the hydrogen separation membrane outlet 6. Moreover, an analysis conducted at the reaction side outlet 7 revealed that the conversion rate of cyclohexane was 70% and 68%, respectively.

Comparative Example 2

The same test as that in Comparative Example 1 was performed except that cyclohexane was used instead of methylcyclohexane.

At first, an analysis conducted at the hydrogen separation membrane outlet 6 after 1 hour from the beginning of the reaction revealed that hydrogen having a purity of 99.9 mole % or more was obtained at a rate of 13.3 L/h. Moreover, an analysis conducted at the reaction side outlet 7 revealed that the conversion rate of cyclohexane was 78%.

The reaction was further continued, and the same analysis was conducted after 100 hours and 300 hours. As a result, hydrogen having a purity of 99.9 mole % or more obtained at the hydrogen separation membrane outlet 6 was reduced to 2.8 L/h after 100 hours and further to 0.6 L/h after 300 hours.

Moreover, an analysis conducted at the reaction side outlet 7 revealed that the conversion rate of cyclohexane was 16% and 4%, respectively.

As is the case with Comparative Example 1, it was found that the initial hydrogen yield was high but activity of the catalyst rapidly decreased in the case where the present invention is not used.

[Examples of the Second Aspect of the Present Invention]

Hereinafter, the second aspect of the present invention will be described in more detail by Examples 11 and 12, but the second aspect of the present invention is not limited to those Examples.

Example 11

Figure 5:
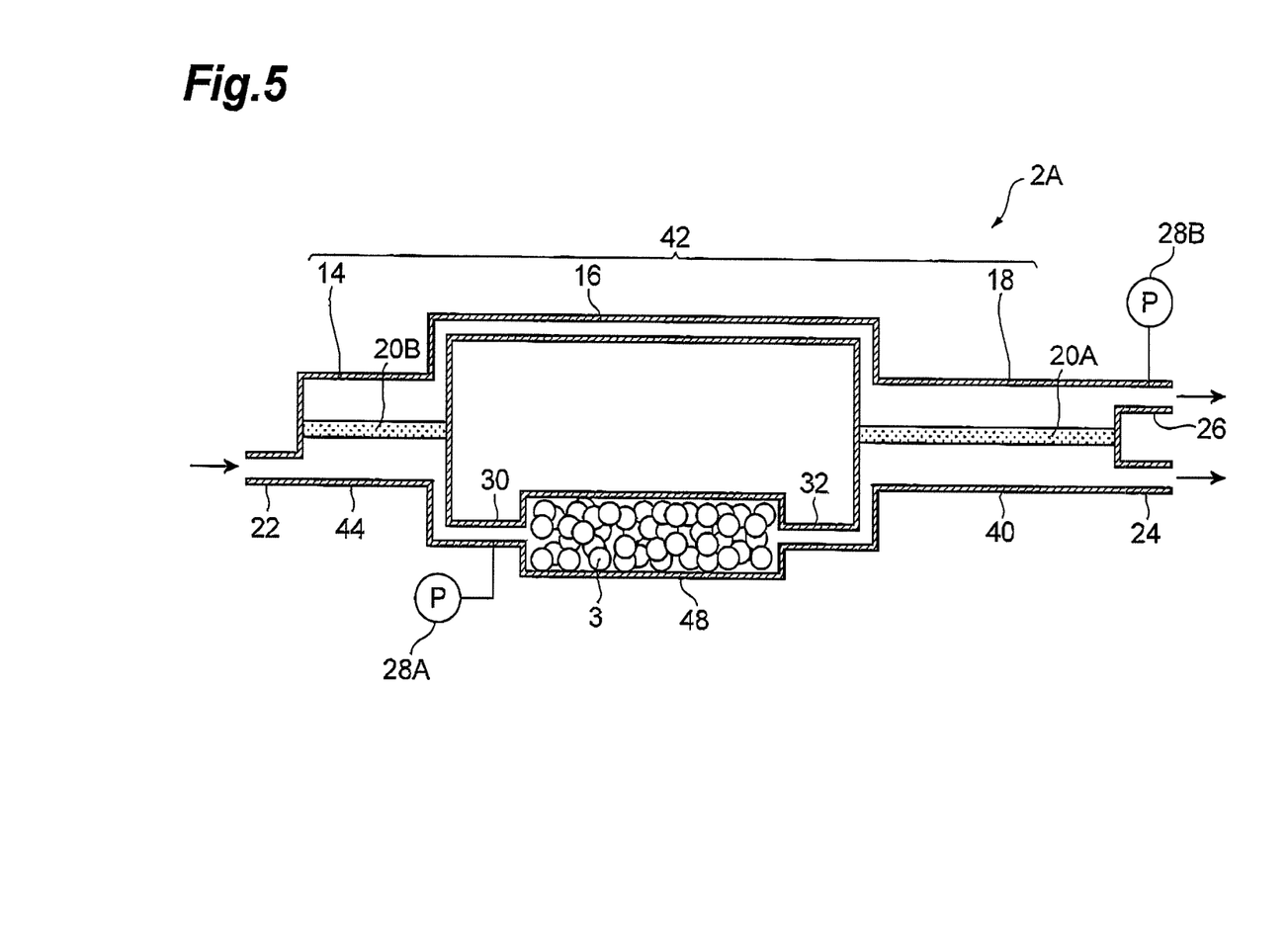
FIG. 5 is a schematic view illustrating a cross section of a hydrogen production apparatus according to a third embodiment of a second aspect of the present invention.

In Example 11, hydrogen was produced by using a hydrogen production apparatus illustrated in FIG. 5. As a reactor 48, a fixed-bed reactor composed of a stainless cylinder having an inner diameter of 25 mm and a length of 100 mm was used. An alumina-supported 2 mass % platinum catalyst having a bulk density of 0.8 and a particle diameter of 1 to 2 mm was packed in the fixed-bed reactor as a dehydrogenation catalyst 3. As a first hydrogen separation membrane 20A and a second hydrogen separation membrane 20B, a plate-shaped hydrogen separation membrane made of a Pd—Ag alloy was used. The thicknesses of the hydrogen separation membranes were set to 60 μm. The area of the second hydrogen separation membrane 20B was set to 50 cm$^2$, The area of the first hydrogen separation membrane 20A was set to 100 cm$^2$. The whole production apparatus 2A was placed in an electrothermal heater. The temperature of the reaction system was measured by a thermocouple installed around an outlet of the reactor 48, and this temperature was controlled as a reaction temperature. The reaction system pressure was measured by a pressure meter 28A. The internal pressure of a hydrogen container 42 was measured by a pressure meter 28B.

Liquid methylcyclohexane was introduced into a reactant container 44 through an introducing pipe 22 at a rate of 33.0 mL/h, and the dehydrogenation reaction of methylcyclohexane was started and a product was measured after 1 hour. It was confirmed that the entire methylcyclohexane was gasified before entering the reactant container 44. The reaction system pressure was maintained at 1 MPa while the dehydrogenation reaction was proceeding, The internal pressure of the hydrogen container 42 was maintained at 0.1 MPa while the dehydrogenation reaction was proceeding. The reaction temperature was maintained at 360° C. while the dehydrogenation reaction was proceeding.

As a result of an analysis at a hydrogen discharging pipe 26, it was confirmed that the product discharged from the hydrogen discharging pipe 26 was hydrogen having a purity of 99.9 mole % or more. The generation rate of hydrogen was 10.3 L/h. It is noted that the generation rate of hydrogen was a value adjusted to the case in which the temperature of hydrogen was 0° C. and the pressure was 1 atm (0.10 MPa). As a result of an analysis at an organic compound discharging pipe 24, it was confirmed that a main product discharged from the organic compound discharging pipe 24 was toluene. The conversion rate of methylcyclohexane was 82%. It is noted that the conversion rate of methylcyclohexane is defined by the following formula (1), when the amount of methyleyclohexane introduced into the reactant container 44 was represented by M1, and the amount of methylcyclohexane remaining in the product discharged from the organic compound discharging pipe 24 was represented by M2.

$$\text{Conversion rate} = \{(M1 - M2)/M1\} \times 100 \quad \text{Formula (1)}$$

After measurement of the product, the dehydrogenation reaction was further continued, and measurement of the product was conducted by the same process as above after 100 hours and 300 hours from the beginning of the reaction. It was confirmed that the products discharged from the hydrogen discharging pipe 26 after 100 hours and 300 hours were hydrogen having a purity of 99.9 mole % or more. The generation rate of hydrogen after 100 hours was 9.4 L/h. The conversion rate of methylcyclohexane after 100 hours was 80%. The generation rate of hydrogen after 300 hours was 8.7 L/h. The conversion rate of methylcyclohexane after 300 hours was 79%.

Comparative Example 11

In Comparative Example 11, the dehydrogenation reaction of methylcyclohexane was conducted by the same process as that in Example 11 except that the second hydrogen separation membrane 20B was replaced by a stainless plate. That is, the hydrogen production apparatus of Comparative Example 11 was not equipped with the second hydrogen separation membrane at an upstream side of the reactor 48. In Comparative Example 11, the product was measured by the same process as that in Example 11.

At each time point after 1 hour, 100 hours, and 300 hours from the beginning of the reaction, it was confirmed that the product discharged from the hydrogen discharging pipe 26 was hydrogen having a purity of 99.9 mole % or more. As a result of an analysis at the organic compound discharging pipe 24, it was confirmed that the main product discharged from the organic compound discharging pipe 24 was toluene.

The generation rate of hydrogen after 1 hour from the beginning of the reaction was 11.0 L/h. The conversion rate of methylcyclohexane after 1 hour was 85%. The generation rate of hydrogen after 100 hours was 7.0 L/h. The conversion rate of methylcyclohexane after 100 hours was 52%. The generation rate of hydrogen after 300 hours was 3.4 L/h. The conversion rate of methylcyclohexane after 300 hours was 28%.

From the result described above, in Comparative Example 11, it was confirmed that the initial yield of hydrogen was high, but activity of the catalyst rapidly decreased in comparison with Example 11.

Example 12

In Example 12, the dehydrogenation reaction of cyclohexane was conducted by the same process as that in Example 11 except that cyclohexane was used instead of methylcyclohexane. In Example 12, the product was measured by the same process as that in Example 11.

At each time point after 1 hour, 100 hours, and 300 hours from the beginning of the reaction, it was confirmed that the product discharged from the hydrogen discharging pipe 26 was hydrogen having a purity of 99.9 mole % or more. As a result of an analysis at the organic compound discharging pipe 24, it was confirmed that the main product discharged from the organic compound discharging pipe 24 was benzene.

The generation rate of hydrogen after 1 hour from the beginning of the reaction was 11.8 L/h. The conversion rate of cyclohexane after 1 hour was 76%. The generation rate of hydrogen after 100 hours was 10.8 L/h. The conversion rate of cyclohexane after 100 hours was 72%. The generation rate of hydrogen after 300 hours was 9.8 L/h. The conversion rate of cyclohexane after 300 hours was 68%. It is noted that the conversion rate of cyclohexane is defined by the following formula (2), when the amount of cyclohexane introduced into the reactant container 44 was represented by C1, and the amount of cyclohexane remaining in the product discharged from the organic compound discharging pipe 24 was represented by C2.

$$\text{Conversion rate} = \{(C1-C2)/C1\} \times 100 \quad \text{Formula (2)}$$

Comparative Example 12

In Comparative Example 12, the dehydrogenation reaction of cyclohexane was conducted by the same process as that in Comparative Example 11 except that cyclohexane was used instead of methylcyclohexane. In Comparative Example 12, the product was analyzed by the same process as that in Comparative Example 11.

At each time point after 1 hour, 100 hours, and 300 hours from the beginning of the reaction, it was confirmed that the product discharged from the hydrogen discharging pipe 26 was hydrogen having a purity of 99.9 mole % or more. As a result of an analysis at the organic compound discharging pipe 24, it was confirmed that the main product discharged from the organic compound discharging pipe 24 was benzene.

The generation rate of hydrogen after 1 hour from the beginning of the reaction was 12.3 L/h. The conversion rate of cyclohexane after 1 hour was 78%. The generation rate of hydrogen after 100 hours was 3.8 L/h. The conversion rate of cyclohexane after 100 hours was 20%. The generation rate of hydrogen after 300 hours was 0.7 L/h. The conversion rate of cyclohexane after 300 hours was 5%.

From the result described above, in Comparative Example 12, it was confirmed that the initial yield of hydrogen was high, but activity of the catalyst rapidly decreased in comparison with Example 12.

INDUSTRIAL APPLICABILITY

According to the first and the second aspects of the present invention, when hydrogen is produced by combining the dehydrogenation reaction of organic hydrides or the like and the hydrogen separation membrane, it is possible to mix hydrogen to the raw material of the dehydrogenation reaction easily and simply and suppress a reduction in activity of the dehydrogenation reaction catalyst easily.

REFERENCE SIGNS LIST

1 . . . reaction container, 2 . . . hydrogen separation membrane, 3 . . . dehydrogenation catalyst, 4 . . . reaction side area, 5 . . . permeation side area, 6 . . . hydrogen separation membrane outlet (hydrogen discharging pipe), 7 . . . reaction side outlet (raw material discharging pipe after dehydrogenation), 8 . . . raw material introducing inlet (raw material introducing pipe), 9 . . . quartz ball, 10 . . . pipe , 11 . . . glass coating, 2A, 2B . . . hydrogen production apparatus, 44 . . . reactant container, 48 . . . reactor, 40 . . . product container, 42 . . . hydrogen container, 14 . . . upstream side hydrogen container, 16, 16 . . . connecting pipe, 16A . . . first connecting pipe, 16B . . . second connecting pipe, 18 . . . downstream side hydrogen container, 20A . . . first hydrogen separation membrane, 20B . . . second hydrogen separation membrane, 22 . . . introducing pipe, 24 . . . organic compound discharging pipe, 26 . . . hydrogen discharging pipe, 28A, 28B . . . pressure meter, 30, 32 . . . pipe.

The invention claimed is:

1. A reactor for dehydrogenation of an organic compound, the reactor being a flow-type reactor, comprising:
   a hydrogen separation membrane selectively permeable to hydrogen; and a dehydrogenation catalyst for promoting a dehydrogenation reaction of an organic compound which can release hydrogen upon the dehydrogenation reaction, and including:

a reaction side area through which the organic compound can flow and which includes the dehydrogenation catalyst; and a permeation side area which is separated from the reaction side area by the hydrogen separation membrane and through which hydrogen that has passed through the hydrogen separation membrane can flow, wherein:

the dehydrogenation catalyst surrounds at least a portion of the permeation side area, and the permeation side area is inward of the dehydrogenation catalyst in a direction toward a longitudinal center of the reactor, the reactor for dehydrogenation of an organic compound including, in this order along a flow direction of the organic compound: a part B in which the hydrogen separation membrane is present and the dehydrogenation catalyst is not present; and a part A in which both of the hydrogen separation membrane and the dehydrogenation catalyst are present.

2. The reactor for dehydrogenation according to claim 1, wherein the dehydrogenation catalyst is not placed upstream of a most upstream edge of the part B along the flow direction of the organic compound.

3. The reactor for dehydrogenation according to claim 1, wherein the organic compound is selected from cyclohexane, methylcyclohexane, decalin, tetralin, 2-propanol, and a mixture thereof.

4. A hydrogen production process using the reactor for dehydrogenation according to claim 1, wherein the following steps are conducted concurrently:

a) a step of transferring hydrogen generated by the dehydrogenation reaction of the organic compound in the reaction side area of the part A to the permeation side area through the hydrogen separation membrane; and b) a step of transferring hydrogen provided to the permeation side area in the step a to the reaction side area of the part B through the hydrogen separation membrane.

5. The reactor for dehydrogenation according to claim 1, further comprising a pipe configured to supply the hydrogen that has passed through the hydrogen separation membrane from the permeation side area to the reaction side area.

* * * * *